US009233187B2

(12) United States Patent
Chun et al.

(10) Patent No.: US 9,233,187 B2
(45) Date of Patent: Jan. 12, 2016

(54) BIODEGRADABLE SUTURE TYPE CELL DELIVERY SYSTEM FOR IMPROVING STEM CELL ENGRAFTMENT RATE

(75) Inventors: Heung Jae Chun, Seoul (KR); Su Jung You, Seoul (KR); Ki Dong Yoo, Seoul (KR); Kyu Nam Park, Seoul (KR); Gue Tae Chae, Seoul (KR); Seok Whan Moon, Seoul (KR); Han Joon Kim, Seoul (KR); Jung Hee Wee, Seoul (KR)

(73) Assignee: Catholic University Industry Academic Cooperation Foundation (KR)

( * ) Notice: Subject to any disclaimer, the term of this patent is extended or adjusted under 35 U.S.C. 154(b) by 1026 days.

(21) Appl. No.: 13/266,677

(22) PCT Filed: Nov. 18, 2009

(86) PCT No.: PCT/KR2009/006795
§ 371 (c)(1),
(2), (4) Date: Dec. 8, 2011

(87) PCT Pub. No.: WO2010/137780
PCT Pub. Date: Dec. 2, 2010

(65) Prior Publication Data
US 2012/0078297 A1 Mar. 29, 2012

(30) Foreign Application Priority Data
May 26, 2009 (KR) .................. 10-2009-0045857

(51) Int. Cl.
*A61B 17/04* (2006.01)
*A61L 17/06* (2006.01)
*A61L 17/00* (2006.01)
*A61L 17/10* (2006.01)
*A61L 17/12* (2006.01)
*A61L 17/14* (2006.01)

(52) U.S. Cl.
CPC ............... *A61L 17/06* (2013.01); *A61L 17/005* (2013.01); *A61L 17/105* (2013.01); *A61L 17/12* (2013.01); *A61L 17/145* (2013.01); *A61L 2300/252* (2013.01)

(58) Field of Classification Search
CPC ............... A61B 17/06166; A61B 2017/00526; A61B 27/58; D02G 3/448
USPC .................................. 606/228–230
See application file for complete search history.

(56) References Cited

U.S. PATENT DOCUMENTS 7,528,105 B1 * 5/2009 Pena et al. ..................... 514/1.1
2006/0002970 A1 * 1/2006 Aspenberg et al. ........... 424/423

FOREIGN PATENT DOCUMENTS

KR       10-0529209 B1   11/2005
KR       10-0782892 B1   12/2007
KR    10-2008-0062252 A    7/2008

OTHER PUBLICATIONS

International Search Report for PCT/KR2009/006795, dated Jul. 29, 2010.

*Primary Examiner* — Gregory Anderson
(74) *Attorney, Agent, or Firm* — Levenfeld Pearlstein, LLC

(57) ABSTRACT

The present invention relates to a biodegradable suture-type cell delivery system, a preparation method thereof and a biodegradable suture comprising the same. The biodegradable suture-type cell delivery system has improved cell compatibility as a result of depositing a hydrophilic functional group-containing compound on the surface of a biodegradable suture yarn made of a biodegradable polymer, a portion of which has partially a bulky structure beneficial for the proliferation of cells or living tissue, so as to hydrophilically modify the surface, and then bonding a cell compatible material to the surface, and also functions as a cell culture scaffold, because the bulky structure is beneficial for the proliferation of cells. Accordingly, the biodegradable suture-type cell delivery system can improve the rate of engraftment of stem cells in vivo.

9 Claims, 7 Drawing Sheets

BIODEGRADABLE SUTURE TYPE CELL DELIVERY SYSTEM FOR IMPROVING STEM CELL ENGRAFTMENT RATE

CROSS-REFERENCE TO RELATED APPLICATIONS

This is a National Stage Application of International Patent Application No. PCT/KR2009/006795, filed Nov. 18, 2009, which claims the benefit of and priority to Korean Patent Application No. 10-2009-0045857, filed May 26, 2009, the contents of each of which are incorporated fully by reference herein.

FIELD OF THE INVENTION

The present invention relates to a biodegradable suture-type cell delivery system, a preparation method thereof and a biodegradable suture comprising the same, and more particularly to a biodegradable suture-type cell delivery system which has improved cell compatibility as a result of depositing a hydrophilic functional group-containing compound on the surface of a biodegradable suture yarn made of a biodegradable polymer, a portion of which has a bulky structure beneficial for the proliferation of cells or living tissue, so as to hydrophilically modify the surface, and then bonding a cell compatible material to the surface, in which the biodegradable suture-type cell delivery system improves the rate of engraftment of stem cells in vivo, and to a method for preparing the biodegradable suture-type cell delivery system and a biodegradable suture comprising the biodegradable suture-type cell delivery system.

DESCRIPTION OF THE PRIOR ART

Treatment of intractable diseases with stem cells is an important issue in the bioscience field in this century and is receiving attention in most fields of medicine, including the cardiovascular system, the nervous system, and blood. Particularly, stem cell therapy is applied even to degenerative diseases considered to be impossible to treat, thereby providing many positive results. From such results, the use of stem cells is estimated as advanced medical technology that can lead to significant changes in clinical practices based on drugs and surgery.

However, therapeutic methods that are performed using stem cells alone have been pointed out to have various problems as indicated in clinical results, and of these problems, the biggest problems are related to targetability and efficiency.

Specifically, study results revealed that conventional injection-type therapeutic agents cannot also be accurately delivered into a target site and that the injected cells can be scattered so that they are difficult to differentiate in a settled state. Thus, as studies on solving the problem associated with the efficiency of stem cell delivery, studies on a method capable of delivering stem cells into a target site to be treated in a stable form have been conducted in various research fields.

As a part of such efforts, hybrid tissue engineering products based on a combination of tissue engineering technology with stem cells are being actively studied. The term "tissue engineering products" refers to introducing a delivery vector into stem cells to take a suitable form of a substance having excellent biocompatibility, and then culturing the stem cells and applying the cultured stem cells to a site in need of therapy. Such tissue engineering products may be manufactured in various forms depending on disease sites.

However, because most biodegradable synthetic polymers that are used in the tissue engineering products are hydrophobic, they need to be treated with a hydrophilic material for tissue engineering applications. In other words, because a scaffold made of a hydrophobic material floats in cell culture media, cells are difficult to proliferate on the scaffold, and the surface treatment of the scaffold should be carried out in advance so that it serves not only as a simple scaffold, but also to increase the proliferation of cells and the function of cells themselves.

Accordingly, the present inventors have made extensive efforts to the utility of a cell culture scaffold made of a hydrophobic material, and as a result, have found that, when the surface of a hydrophobic biodegradable synthetic polymer is first modified with a hydrophilic material so as to enable the introduction of a functional group for secondary modification onto the surface and a cell compatible material is then bonded to the surface, the cell compatibility of the polymer can be increased and the polymer can function as a cell culture scaffold, because the bulky structure is beneficial for the proliferation of cells or living tissue, thereby completing the present invention.

SUMMARY OF THE INVENTION

It is an object of the present invention to provide a biodegradable suture-type cell delivery system obtained by hydrophilically modifying the surface of a hydrophobic biodegradable suture, a portion of which has partially a bulky structure, and then bonding a cell compatible material to the surface, and a preparation method thereof.

Another object of the present invention is to provide a biodegradable suture for improving the rate of engraftment of stem cells in vivo, which is obtained by hydrophilically modifying the surface of a hydrophobic biodegradable suture having a bulky structure and then bonding a cell compatible material to the surface.

To achieve the above objects, the present invention provides a biodegradable suture-type cell delivery system obtained by depositing a hydrophilic functional group-containing compound to the surface of a hydrophobic biodegradable suture made of a biodegradable polymer, a portion of which has partially a bulky structure, so as to hydrophilically modify the surface, and then bonding a cell compatible material to the surface.

The biodegradable suture-type cell delivery system of the present invention functions as a cell culture scaffold, because the bulky structure is beneficial for the proliferation of cells or living tissue. Particularly, the biodegradable suture-type cell delivery system of the present invention improves the rate of engraftment of stem cells in vivo.

The biodegradable suture-type cell delivery system of the present invention comprises a multifilament draw-textured yarn made of a biodegradable polymer, a portion of which has partially a bulkiness of 150-1000%, in which the biodegradable multifilament draw-textured yarn having the bulky structure has pores of 1-150 μm.

The biodegradable polymer that is used in the present invention is preferably a homopolymer or a copolymer comprising a compound selected from the group consisting of glycolide, glycolic acid, lactide, lactic acid, caprolactone, dioxanone, trimethyl carbonate, and ethyl glycol, and more preferably a copolymer of glycolide and lactide (90:10 to 70:30 w/w).

In the biodegradable suture type cell delivery system of the present invention, the hydrophilic functional group-containing compound comprises any one hydrophilic functional group selected from the group consisting of an amine group (—NH$_2$), a carboxylic group (—COOH) and a hydroxyl group (—OH). More preferably, the hydrophilic functional group-containing compound is a hydrophilic amine compound.

The cell compatible material that is used in the present invention may be an extracellular matrix that can induce the adhesion and proliferation of cells and can affect the intrinsic function of cells or comprises a motif including a peptide (RGD). In a preferred embodiment, the cell compatible material may be any one selected from the group consisting of collagen, gelatin, laminin, fibronectin, galactose and chitosan.

The present invention also provides a method for preparing said biodegradable suture-type cell delivery system. More specifically, the preparation method comprises the steps of: imparting a bulky structure to a portion of a multifilament draw-textured yarn made of a biodegradable polymer; twisting or braiding the multifilament draw-textured yarn having the bulky structure to improve the cohesion of the yarn; depositing a hydrophilic functional group-containing compound on the surface of the multifilament draw-textured yarn having the bulky structure by a plasma enhanced chemical vapor deposition process; and bonding a cell compatible material to the surface using a coupling agent after the depositing step.

In the preparation method, the diameter of the single yarn in the multifilament draw-textured yarn is 5 to 30 μm, and the diameter of the plied yarn in the multifilament draw-textured yarn is 40 to 1000 μm.

Also, a portion of the multifilament draw-textured yarn that is used in the preparation method of the present invention has a bulkiness of 150-1000%, and the multifilament draw-textured yarn having the bulky structure has pores of 1-150 μm.

In the preparation method of the present invention, the hydrophilic functional group-containing compound are deposited by the plasma enhanced chemical deposition process under the conditions of low pressure of 25 mtorr or less and power of 50-100 W. The hydrophilic functional group in the hydrophilic functional group-containing compound that is used in the present invention is any one selected from the group consisting of an amine group (—NH$_2$), a carboxyl group (—COOH) and a hydroxyl group (—OH).

The cell compatible material that is used in the present invention may be an extracellular matrix that can induce the adhesion and proliferation of cells and can affect the intrinsic function of cells or comprises a motif including a peptide (RGD). In a preferred embodiment, the cell compatible material is any one selected from the group consisting of collagen, gelatin, laminin, fibronectin, galactose and chitosan. In examples of the present invention, galactose or collagen was used as the cell compatible material, but is not limited thereto.

Further, the present invention provides a biodegradable suture obtained by depositing a hydrophilic functional group-containing compound on the surface of a multifilament draw-textured yarn (hereinafter referred to as "multifilament DTY"), a portion of which has partially a bulkiness of 150-1000% and pores of 1-150 μm, and then bonding a cell compatible material to the surface.

Herein, the biodegradable polymer that is used in the present invention is a copolymer of glycolide and lactide (90:10 to 70:30 w/w).

More specifically, the present invention provides a biodegradable suture obtained by depositing a hydrophilic amine compound on the surface of a biodegradable multifilament DTY and then bonding collagen as a cell compatible material to the surface.

According to the present invention, the biodegradable suture-type cell delivery system may be provided by hydrophilically modifying the surface of the hydrophobic biodegradable suture made of the biodegradable polymer and then bonding a cell compatible material to the surface. Particularly, the biodegradable suture of the present invention has a structure of the multifilament draw-textured yarn having the bulky structure in which cells or living tissues are to proliferate.

In addition, the present invention may provide a cell compatible suture which has improved cell compatibility as a result of hydrophilically modifying the surface of a hydrophobic biodegradable suture made of a biodegradable polymer having a bulky structure, and at the same time, improves the rate of engraftment of stem cells in vivo.

BRIEF DESCRIPTION OF THE DRAWINGS

The above and other objects, features and advantages of the present invention will be more clearly understood from the following detailed description taken in conjunction with the accompanying drawing, in which.

DETAILED DESCRIPTION OF THE INVENTION

Hereinafter, the present invention will be described in detail.

The present invention provides a biodegradable suture-type cell delivery system which is obtained by depositing a hydrophilic functional group-containing compound on the surface of a hydrophobic biodegradable suture made of a biodegradable polymer, a portion of which has partially a bulky structure, so as to hydrophilically modify the surface, and then bonding a cell compatible material to the surface, such that cells or living tissues proliferate in the bulky structure.

The biodegradable suture-type cell delivery system of the present invention comprises a multifilament draw-textured yarn (DTY) made of a biodegradable polymer and has bulkiness and excellent soft feeling which are the natural properties of DTY. Furthermore, according to the present invention, a bulky structure is imparted to a portion of the multifilament draw-textured yarn, such that, when it is used in medical applications, it is suitable for cell culture, cell delivery or drug delivery due to the bulky structure.

As used herein, the term "bulky structure" refers to a structure in which a plurality of pores having a size of 1 µm or more exist between fibers, and the term "bulkiness" means that a portion of a multifilament draw-textured yarn made of a biodegradable polymer is imparted with a bulkiness of 150-1000%, and more preferably 200-600%, by stretching or drawing, and additionally twisting or braiding.

Specifically, the multifilament draw-textured yarn of the present invention has a bulky structure having pores of 1-150 µm, and preferably 5-50 µm. Thus, in the multifilament draw-textured yarn, it is easy to form open structures between pores due to high porosity.

The bulkiness of the multifilament draw-textured yarn of the present invention can be freely controlled depending on applications and subjects, including cell culture, cell delivery or drug delivery. However, if the bulkiness is less than 150%, pores between yarns will become smaller, and thus cell proliferation during cell culture will be difficult and the content of cells or drugs that can be delivered into a living body will decrease, so that the utility of the draw-textured yarn as a scaffold will decrease. On the other hand, if the bulkiness is more than 1000%, the occurrence of yarn breakage will increase due to the low durability of the biodegradable polymer resin, and the pores between yarns will become excessively larger so that the ability to retain cells or drugs will decrease.

Figure 1:
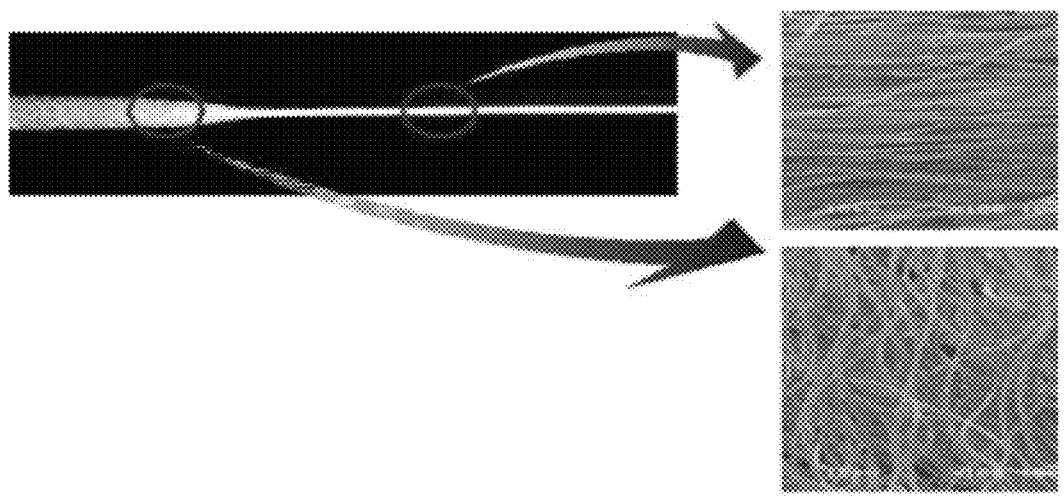
FIG. 1 is an enlarged scanning electron micrograph of a biodegradable multifilament draw-textured yarn having a bulky structure according to the present invention.

FIG. 1 is an enlarged scanning electron micrograph of a biodegradable multifilament draw-textured yarn having a bulky structure according to the present invention. As can be seen therein, the biodegradable draw-textured yarn of the present invention has a network structure having pores within the bulky structure. The bulkiness or pore size of the bulky structure can be controlled according to stretching or drawing conditions during the preparation of the draw-textured yarn.

It is to be understood that the pore size can be suitably controlled depending on the size of cell or drug selected. More specifically, the bulky structure of the multifilament draw-textured yarn according to the present invention has a pore size of 10150 µm, and preferably 5-50 µm. If the pore size is less than 1 µm, pores between yarns will become smaller, and thus cell proliferation during cell culture will be difficult and the content of cell or drug that can be delivered into a living body will decrease, so that the utility of the draw-textured yarn for medical applications will decrease. On the other hand, if the pore size is more than 150 µm, the pores between yarns will becomes excessively larger so that the ability of the draw-textured yarn to retain a drug is likely to decrease.

In the present invention, the bulky multifilament draw-textured yarn for delivering a cell or a drug into a living body is preferably degraded and absorbed in vivo after achieving its purpose, and thus is preferably made of a biodegradable polymer.

As the biodegradable polymer that is used in the present invention, a biodegradable aliphatic polyester satisfying biocompatibility and biodegradability may be used without particular limitation. In a preferred embodiment, the biodegradable polymer is a homopolymer or a copolymer comprising a compound selected from the group consisting of glycolide, glycolic acid, lactide, lactic acid, caprolactone, dioxanone, trimethyl carbonate and ethylene glycol.

More preferably, the biodegradable polymer is a poly(DL-lactide-co-glycolide) acid (hereinafter referred to as "PLGA") that is a copolymer of glycolide and lactide (90:10 to 70:30 w/w). In examples of the present invention, a copolymer of glycolide and lactide (90:10 w/w) was used as the biodegradable polymer resin, but is not limited thereto.

To prepare the hydrophilically surface-modified biodegradable suture-type cell delivery system, a compound containing any one hydrophilic functional group selected from the group consisting of an amine group ($-NH_2$), a carboxylic group ($-COOH$) and a hydroxyl group ($-OH$) is first deposited on the surface of the hydrophobic biodegradable multifilament draw-textured yarn (DTY).

Herein, the hydrophilic functional group-containing compound that is used in the present invention is preferably a hydrophilic amine compound. In examples of the present invention, allylamine was used, but is not limited thereto.

Particularly, in the biodegradable suture-type cell delivery system of the present invention, after the surface of the biodegradable multifilament draw-textured yarn (DTY) has been modified with the hydrophilic functional group-containing compound, a cell compatible material is bonded to the surface, whereby the cell compatibility of the textured yarn can be improved so that cells can stably proliferate on the textured yarn. Also, the bulky structure of the textured yarn is beneficial for the proliferation of cells or living tissue, and thus the textured yarn functions as a cell culture scaffold.

As used herein, the term "cell compatible material" refers to a material that can induce the adhesion and proliferation of cells and can influence the intrinsic function of cells or includes a motif including a peptide (RGD). The cell compatible material satisfying such requirements may be used without limitation in the present invention. Preferably, the cell compatible material may be any one selected from the group consisting of collagen, gelatin, laminin, fibronectin, galactose and chitosan.

The present invention provides a method for preparing a biodegradable suture-type cell delivery system, the method comprising the steps of: (1) imparting a bulky structure to a portion of a multifilament draw-textured yarn (DTY) made of a biodegradable polymer; (2) twisting or braiding the multifilament draw-textured yarn having the bulky structure to increase the coherence of the yarn; (3) depositing a hydrophilic functional group-containing compound on the surface of the multifilament draw-textured yarn having the bulky structure by a plasma enhanced chemical vapor deposition process; and (4) bonding a cell compatible material to the surface using a coupling agent after the depositing step.

Hereinafter, each step of the preparation method according to the present invention will be described in detail.

In step (1) of the method of the present invention, a biodegradable polymer is spun through a spinneret to prepare an ultrafine multifilament yarn having a single-yarn diameter of 5-30 µm. Herein, the ultrafine multifilament yarn satisfies a tenacity of 2.0-9.0 g/d and an elongation of 20-80% such that the occurrence of yarn blockage and deterioration in quality during a subsequent draw-texturing process can be minimized. If the elongation of the multifilament yarn is less than 20%, the texturing workability of the yarn will be rapidly deteriorated due to high tension, and the higher the elongation, the better is the workability; however, if the elongation of the multifilament yarn is more than 80%, the workability thereof will be significantly reduced. More preferably, the multifilament yarn has an elongation of 25-40%. Also, if the tenacity of the multifilament yarn is less than 2.0 g/d, the texturing workability will decrease, and if it is higher than 9.0 g/d, the soft touch of the draw-textured yarn will be reduced.

Meanwhile, if the single-yarn diameter of the multifilament draw-textured yarn is more than 30 μm, the degradation rate of the yarn after cell culture, cell delivery or drug delivery can become slower, and the stiffness of the yarn will increase so that the workability or convenience of use of the yarn will decrease.

The single-yarn diameter of the prepared multifilament draw-textured yarn can vary depending on the application field and intended use of the yarn, and if the yarn is applied to a medical suture, the diameter of the plied yarn is preferably 40-1000 μm, and more preferably 40-800 μm.

If the diameter of the plied yarn is less than 40 μm, yarn breakage will be likely to occur during the stretching/draw-twisting process and the efficiency of production of the bulky structure will be low, and the tenacity of the yarn will be low, leading to a decrease in the convenience of implantation. If the diameter of the plied yarn is more than 1000 μm, it will be difficult to apply the yarn in vivo by a surgical operation using a conventional suturing technique, and the foreign body reaction of the polymer used in vivo will be increased.

Subsequently, the plied multifilament yarn is subjected to a draw-texturing process to prepare a multifilament draw-textured yarn. In order to ensure the texturing workability and the quality of the draw-textured yarn, the draw-texturing process is carried out at a linear velocity of 200-700 m/min, and preferably 250-400 m/min, at a drawing ratio of 1.01-1.8, and preferably 1.02-1.7.

In step (1) of the preparation method of the present invention, the multifilament draw-textured yarn prepared as described above is stretched or drawn to impart a bulky structure to the draw-textured yarn.

In step (1), a process of imparting the bulky structure is carried out by winding the biodegradable multifilament draw-textured yarn on a stretchable rack, and then stretching the wound yarn by 3-10%, and preferably 4-7%. If the stretch ratio is less than 3%, it will be difficult to make the bulky structure, and if it will exceed 10%, yarn breakage will be likely to occur. Another process of imparting the bulky structure is carried out by a drawing method in a continuous process.

Step (2) of the preparation method of the present invention is a step of twisting or braiding the multifilament draw-textured yarn having the bulky structure formed in step (1).

The twisting or braiding process is carried out in order to improve the cohesion, mechanical properties and use convenience of the multifilament draw-textured yarn having the bulky structure. After the process of imparting the bulky structure, the multifilament draw-stretched yarn is separated from the rack, and then twisted at 200 turns/meter or less in order to maintain the bulky structure while enhancing the cohesion of the yarn.

Meanwhile, if the biodegradable multifilament draw-textured yarn having the bulky structure is used as a suture, a braiding process may be used instead of the twisting process. The braiding process is carried out in such a manner that a predetermined portion is not braided so as to retain a bulky structure in a portion of the yarn.

The biodegradable multifilament draw-textured yarn of the present invention having the bulky structure manufactured through the above-described steps has a bulky structure including pores of 1-150 μm in diameter, and preferably 5-50 μm in diameter. The size of pores in the bulky structure is easily controlled, and the bulky structure shows high porosity.

Step (2) of the method of the present invention may additionally comprise a coating process for a portion of the twisted or braided multifilament draw-textured yarn to further enhance the cohesion of the yarn and to reduce damage to biological tissue during the use of the yarn.

By additionally imparting cohesion to only a portion of the bulky multifilament draw-textured yarn through the twisting or braiding process and the coating process, a bulkiness of 150-1000%, and preferably 200-600% is imparted to the incoherent portion of the multifilament draw-textured yarn.

Specifically, in the coating process, a coating solution containing 1-10 wt % of a biodegradable polymer resin in an organic solvent is applied to the twisted or braided multifilament draw-textured yarn by a conventional method such as application or impregnation.

Herein, the biodegradable polymer resin which is used in the coating solution to form a film layer on the yarn surface is a homopolymer or a copolymer comprising a compound selected from the group consisting of glycolide, glycolic acid, lactide, lactic acid, caprolactone, dioxanone, trimethylene carbonate and ethylene glycol, or is a biodegradable natural polymer selected from the group consisting of collagen, cellulose oxide, chitosan, gelatin, fibrin, hyaluronic acid and alginate. Preferably, either a copolymer of glycolide and lactide (30:70) or polycaprolactone is dissolved in ethylene acetate or methylene chloride and used as the coating resin. Also, for the convenience of implantation, a softener such as calcium stearate may be added to the coating solution.

Step (3) of the method according to the present invention is a step of depositing a hydrophilic functional group-containing compound on the surface of the multifilament draw-textured yarn having the bulky structure by a plasma enhanced chemical vapor deposition process.

In the surface modification by the plasma enhanced chemical vapor deposition process, a radical is produced on the polymer surface having no reactive group, and then the linked portion of the produced radical is broken, whereby the surface is polymerized with the compound containing the hydrophilic functional group to be treated on the surface.

Particularly, because PLGA that is used as a preferred biodegradable polymer in the present invention has low heat resistance, the surface modification is preferably carried out by the plasma enhanced chemical vapor deposition process.

Using the plasma enhanced chemical vapor deposition process, the hydrophilic functional group-containing compound can be deposited on the surface of the textured yarn under the conditions of low pressure of 25 mtorr or less and power of 50-100 W.

The vapor deposition employs a phenomenon in which, when gases and organic vapors are converted from a low-pressure state to plasma, a polymer is produced while it covers the surrounding solid surface to form a thin film. In the vapor deposition, a gas or an organic solvent is electrically discharged in a low-pressure state. Thus, lower pressures are preferred, and in examples of the present invention, a pressure of 25 mTorr was used, but is not limited thereto.

Unlike a conventional chemical vapor deposition process in which power is determined by deposition rate, if the power in the plasma enhanced chemical vapor deposition process of the present invention is more than 100 W, the generated gases and organic vapors will be dissociated by plasma, and thus the power can result in a decrease in deposition rate or no longer have an effect on deposition.

The thickness of deposition by plasma enhanced chemical vapor deposition can be controlled according to power and treatment time, but if an amine-based monomer that is strongly toxic is converted to a polymer during the deposition process, the polymer will not be toxic. Thus, when an amine compound is used as the hydrophilic functional group-containing compound, the thickness of deposition is preferably controlled such that it does not exceed 100□.

Step (4) of the method of the present invention is a step of bonding a cell compatible material to the surface of the textured yarn using a coupling agent after the deposition step.

The coupling agent that is used in the present invention may be one that can cause condensation with a —NH$_2$ group and a —COOH group. A preferred example of the coupling agent is 1-ethyl-3-(3-dimethylamino propyl)carbodiimide (EDC) or N-hydroxysuccimide (NHS).

FIGS. 2 to 6 show the results of measuring the change in chemical structure caused by surface treatment of the biodegradable multifilament draw-textured yarn having the bulky structure according to the present invention. From the results of FTIR-ATR in FIG. 2, the bond of the hydrophilic group-containing compound can be seen, and from the results of ESCA measurement in FIGS. 3 to 5, the bond of the hydrophilic group-containing compound and the adhesion of the cell compatible material can be seen.

Figure 6:
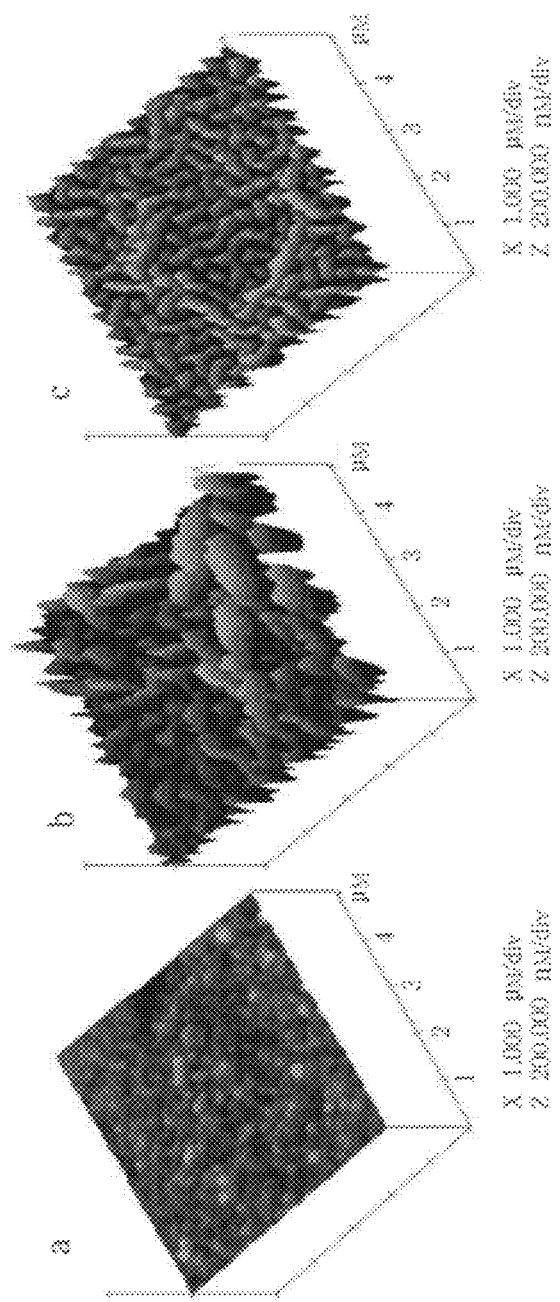
FIG. 6 shows the results of AFM measurement of the surface roughness caused by surface treatment of a biodegradable multifilament draw-textured yarn having a bulky structure according to the present invention.

As can be seen in FIG. 6, the results of measuring the surface roughness using AFM indicate that the surface roughness of the yarn surface-treated with the hydrophilic group-containing compound is higher than that of non-surface-treated PLGA and is decreased as the cell compatible material i.e. galactose is subsequently bonded to cover the surface.

Furthermore, the present invention provides a biodegradable suture obtained by depositing a hydrophilic functional group-containing compound on a biodegradable multifilament draw-textured yarn (DTY), a portion of which has a bulkiness of 150-1000% and pores of 1-150 μm, and then bonding a cell compatible material to the surface.

The biodegradable suture of the present invention is made of a PLGA material that is a copolymer of glycolide and lactide (90:10 to 70:30 w/w).

PLGA that is used in the present invention is biodegradable by heat and moisture, and the biodegradation time thereof can be controlled according to the ratio of polylactic acid (PLA) to polyglycolide (PGA).

The degradation time of PGA is as short as about 3 months, and because the degradation time of PGA is substantially consistent with the cure time of a damage skin, PGA can be used as a surgical suture. However, it has been pointed out to have problems in that it is stiff, and thus it is difficult to knot during a surgical operation and is easily disentangled. Meanwhile, PLGA that is a new suture material made of a copolymer of PGA and PLA has low cell compatibility, because both PLA and PGA are prepared from ultra-hydrophobic synthetic materials. However, the inventive suture made of PLGA has improved cell compatibility, because the hydrophilic functional group-containing compound is first deposited on the surface of PLGA so as to enable secondary modification, after which the cell compatible material is bonded to the surface.

Particularly, the biodegradable suture obtained by depositing a hydrophilic amine compound as the hydrophilic functional group-containing compound on the surface of the textured yarn and introducing collagen as the cell compatible material onto the surface has excellent biocompatibility due to improved cell compatibility. Specifically, in examples of the present invention, allylamine was used as the hydrophilic amine compound, but is not limited. Also, collagen was used as the cell compatible material, but it will be understood that the cell compatible material can vary according to the type of cell or drug delivery system.

Figure 7:
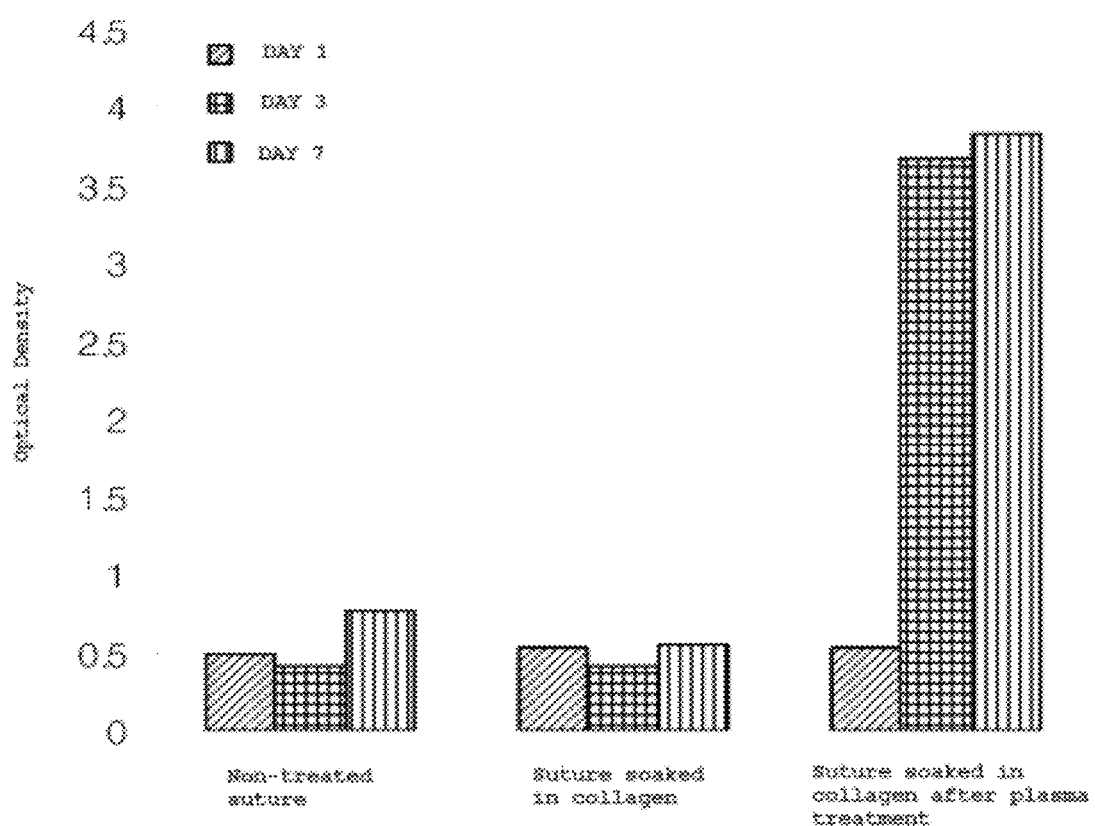
FIG. 7 shows the results of cell proliferation after surface treatment of a biodegradable suture having a bulky structure according to the present invention.

FIG. 7 shows the results of cell proliferation after surface treatment of the biodegradable suture having the bulky structure according to the present invention. As can be seen therein, from the difference in optical density between the inventive suture surface-modified by plasma treatment, a non-treated suture and a suture simply soaked in collagen, a significant increase in the ability of cell proliferation on the surface-modified suture can be confirmed.

Figure 8:
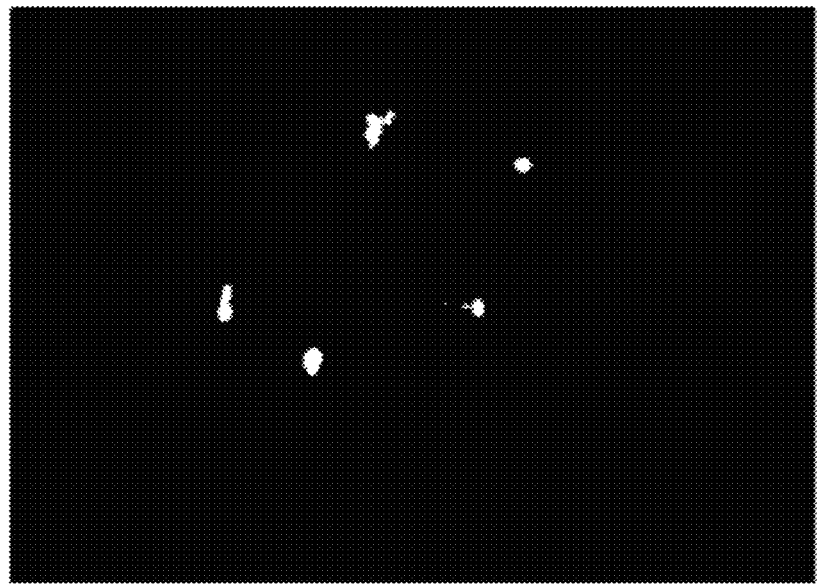
FIG. 8 is a photograph showing cell proliferation at one week after cell culture on a non-surface-treated biodegradable suture.
Figure 9:
FIG. 9 is a photograph showing cell proliferation at one week after cell culture on a surface-treated biodegradable suture having a bulky structure according to the present invention.

As shown in FIGS. 8 and 9, when cells are labeled with a green fluorescent protein (GFP) and then observed, it can be seen that the cells survive better on the inventive suture surface-modified with collagen by plasma treatment than on the non-treated suture.

Hereinafter, the present invention will be described in further detail with reference to examples. It is to be understood, however, that these examples are for illustrative purposes only and are not to be construed to limit the scope of the present invention.

EXAMPLE 1

Surface Treatment of PLGA Draw-Textured Yarn Having Bulky Structure

Step 1: Preparation of PLGA Having Bulky Structure

Poly(glycolide-co-lactide) (hereinafter referred to as "PLGA") consisting of glycolide and lactide at a weight ratio of 90:10 was spun by a conventional method to prepare a multifilament yarn consisting of 56 filaments each having a diameter of 15-17 μm.

The prepared multifilament yarn was plied and heat-treated using Murata 33H (belt type; belt angle 110°), thus preparing a draw-textured yarn (DTY).

Four bundles of the prepared multifilament yarn were plied using Murata 33H (belt type; belt angle 110°), while they were twisted on the first roller in the Z-direction, untwisted on the second roller, and then heat-set at 170° C., thus preparing a draw-textured yarn (DTY) consisting of 224 filaments. The draw-texturing process was performed at a draw ratio of 1.024 and a linear velocity of 250 m/min.

Then, the draw-textured yarn made of poly(glycolide-co-lactide) was wound on a stretchable rack, and then stretched by 4%, thus preparing a multifilament draw-textured yarn having a bulky structure.

The prepared bulky multifilament draw-textured yarn was separated from the rack, and then twisted at 80 turns/meter. The twisted multifilament draw-textured yarn was cut to a length of 45 cm, and the remainder other than about 5 cm of the central portion of the cut yarn was coated under tension such that the yarn was stretched by about 4%. Then, the coated yarn was dried for about 3 seconds in a hot-air dryer at 40° C. The coating process was carried out using a coating solution containing 2 wt % of a copolymer of glycolide and lactide (30/70 w/w) in ethylene acetate.

Step 2: Surface Treatment of Suture

In order to modify the surface of the PLGA draw-textured yarn prepared in step 1, the PLGA draw-textured yarn was well fixed in a plasma enhanced chemical vapor deposition (PECVD) chamber, after which vaporized allylamine (KANTO CHEMICAL CO., INC. Japan) was deposited on the surface of the yarn to a thickness of 100 Å under the conditions of pressure of 25 mtorr and powder of 50 W.

Then, collagen (BD, USA) was introduced into the allylamine-grafted PLGA draw-textured yarn (PLGA-g-AA) using 10 mg of the coupling agents NHS (Fluka, China) and EDC (Sigma, USA)).

EXAMPLE 2

The procedure of Example 1 was repeated, except that galactose was used instead of collagen.

Test Example 1

Surface Analysis

In order to observe the surface of the PLGA draw-textured yarn prepared in Example 2, Fourier transform infrared spectroscopy in the attenuated total reflectance (FTIR-ATR), electron spectroscopy of chemical analysis (ESCA) using the photoelectric effect of X rays, atomic force microscopy (AFM), and the measurement of contact angle by goniometry were performed.

Also, in order to observe a change in functional groups on the surface after deposition of allylamine and the secondary material, infrared spectroscopy was performed using the Nicolet AVATAR 360 spectrometer (WI, USA). In addition, in order to measure the elementary composition of the surface, electron spectroscopy of chemical analysis (ESCA) was performed using the Physical Electronic PHI 5800 ESCA system (Physical Electronics Inc., MN, USA).

1. Results of FTIR-ATR Measurement

A reaction for surface treatment of the biodegradable multifilament draw-textured yarn having the bulky structure, prepared in Example 2, is shown in the following reaction scheme 1:

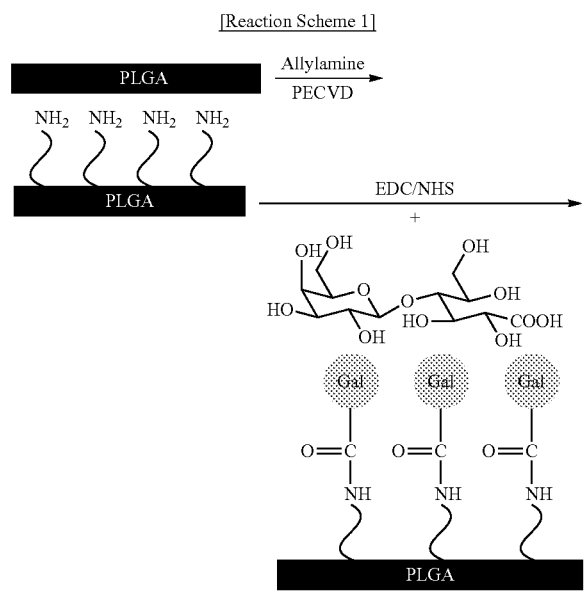

[Reaction Scheme 1]

Figure 2:
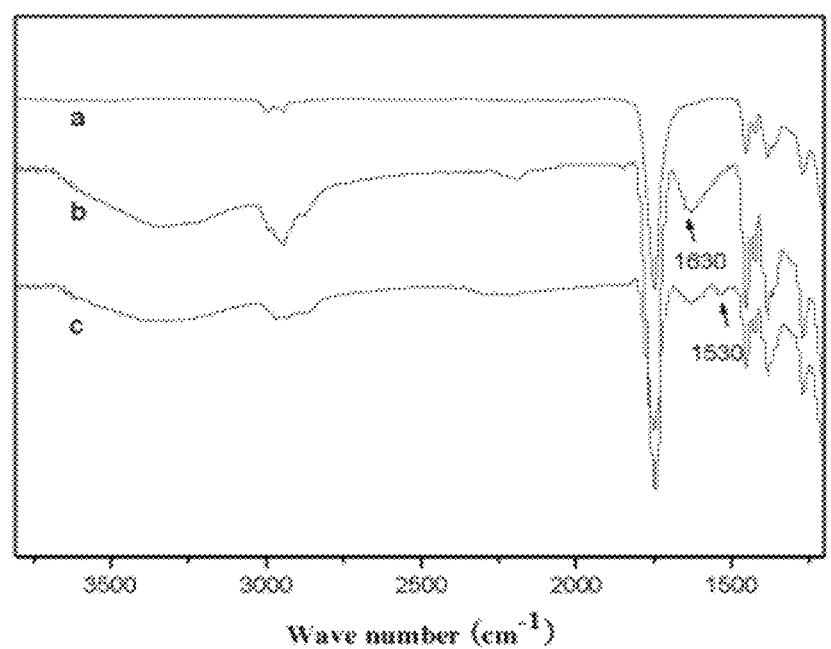
FIG. 2 shows the results of FTIR-ATR measurement of a change in the chemical structure caused by surface treatment of a biodegradable multifilament draw-textured yarn having a bulky structure according to the present invention.

FIG. 2 shows the results of FTIR-ATR measurement of a change in chemical structure caused by surface treatment of the biodegradable multifilament draw-textured yarn having the bulky structure, prepared in Example 2 of the present invention. In FIG. 1, "a" is the characteristic peak of PLGA, and a peak of 1750 cm$^{-1}$, a carbonyl group in the main chain of PLGA, can be seen, and a methyl peak can be seen at 1452, 1380 and 1269 cm$^{-1}$. "b" shows the results obtained after primary surface treatment with allylamine, and new peaks are seen at around 1630 cm and 3000-3500 cm$^{-1}$, indicating the grafting reaction of allylamine. As can be seen in "c", the reaction peak of allylamine is maintained even after introduction of collagen after the amine group was bound, suggesting that the cell compatible material can be stably introduced into the yarn.

2. Results of ESCA Measurement

Figure 3:
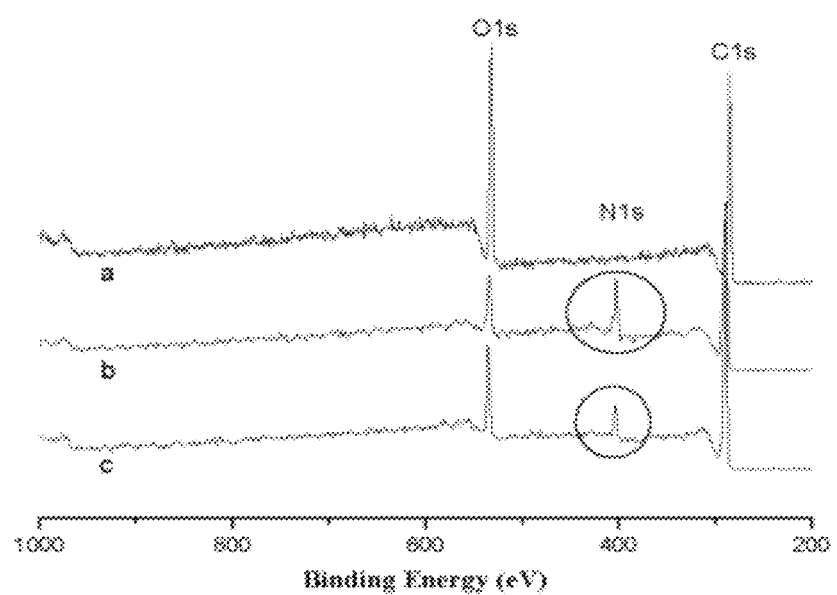
FIG. 3 shows the results of ESCA measurement of a change in the chemical structure caused by surface treatment of a biodegradable multifilament draw-textured yarn having a bulky structure according to the present invention.

FIG. 3 shows the results of ESCA measurement of a change in chemical structure caused by surface treatment of the biodegradable multifilament draw-textured yarn having the bulky structure, prepared in Example 2 of the present invention. In FIG. 3, "a" is the peak of PLGA itself, "b" shows the results of surface treatment with allylamine (AA), and "c" shows the results of surface treatment with allylamine (AA) and galactose (LA). The generation of a new peak at around 400 eV can be seen in FIG. 3. This peak is one generated by the carbon and nitrogen groups of allylamine.

Figure 4:
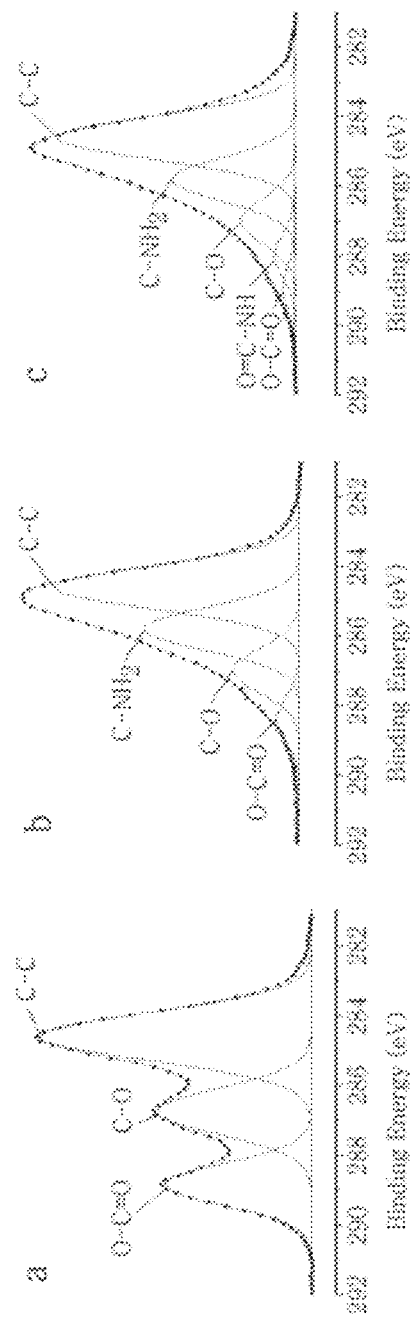
FIG. 4 shows the C1s peak of PLGA modified by surface treatment, in the ESCA measurement of FIG. 3.
Figure 5:
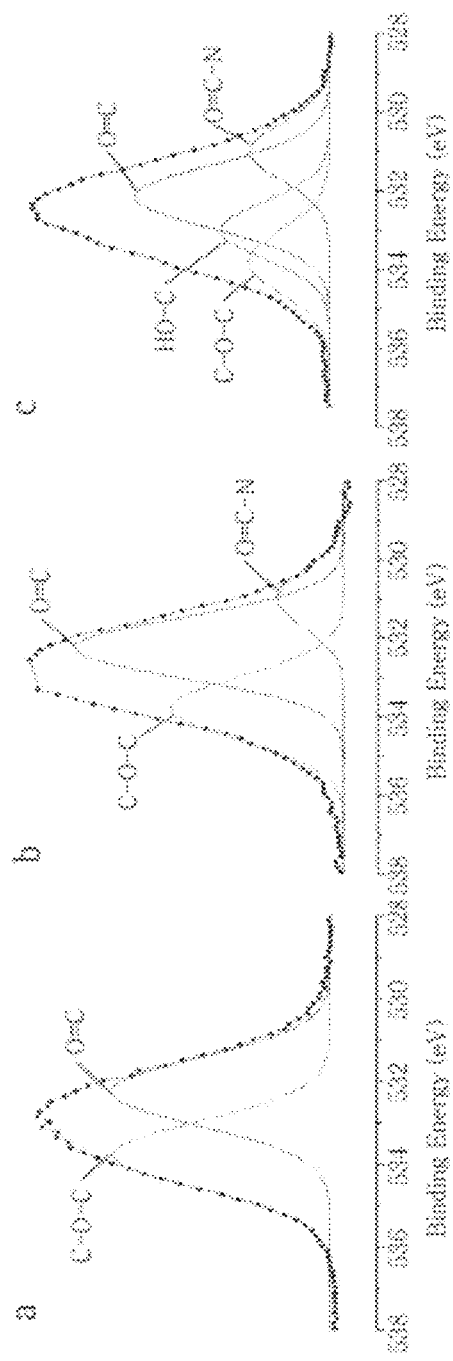
FIG. 5 shows the O1s peak of PLGA modified by surface treatment, in the ESCA measurement of FIG. 3.

FIG. 4 shows the C1s peak of PLGA modified by surface treatment, in the ESCA measurement of FIG. 3, and FIG. 5 shows the O1s peak of PLGA modified by surface treatment, in the ESCA measurement of FIG. 3.

As a result, it can be seen that the pattern of the peak differs between the graphs for the yarns treated with allylamine and galactose. Specifically, when the yarn was surface-treated, O=C—NH and HO—C bonds which could not be seen in the case of surface treatment with galactose were newly formed. These new bonds cannot be produced by treatment with allylamine alone and suggest that the yarn surface is primarily treated with allylamine after which it is successfully treated with galactose.

3. Results of Atomic Force Microscopy (AFM)

FIG. 6 shows the results of AFM for the surface roughness caused by surface treatment of the biodegradable multifilament draw-textured yarn having the bulky structure, prepared in Example 2 of the present invention. As can be seen therein, the surface roughness of non-treated PLGA was measured to be 1.639 nm, whereas the surface roughness values of the samples treated with allylamine and with allylamine and galactose were measured to be 21.392 nm and 12.555 nm, respectively.

Thus, it appears that primary treatment with allylamine resulted in a significantly rough surface, after which the surface roughness was reduced as the surface was covered by galactose.

4. Results of Contact Angle

After surface treatment of the biodegradable multifilament draw-textured yarn having the bulky structure, prepared in Example 2, the contact angles and surface tensions of non-treated PLGA, the PLGA surface-treated with allylamine (AA), and the PLGA surface-treated with allylamine (AA) and galactose (LA) were measured, and the results of the measurement are shown in Table 1 below.

TABLE 1

Results of measurement of contact angle

| Samples | Contact angle (°) | Surface tension (mJ/m$^2$) |
|---|---|---|
| PLGA | 67.50 | 39.95 |
| PLGA-g-AA | 54.49 | 41.10 |
| PLGA-g-AA/LA | 60.72 | 38.72 |

As can be seen from the results in Table 1 above, in the case of the PLGA films treated with allylamine and with allylamine followed by galactose, the contact angle was reduced, suggesting that the surfaces of the PLGA films were well treated with allylamine and galactose by the hydrophilic functional groups (—NH$_2$, —COOH and —OH) present on the surface.

The above surface analysis results revealed that the surface of the biodegradable suture (PLGA) which was primarily modified with reactive groups by the direct vapor deposition process according to the present invention can be secondarily modified with another material.

Thus, in the case of Example 1 of the present invention, after the surface of the biodegradable suture (PLGA) was primarily modified with allylamine and then secondarily modified with collagen, the adhesion and proliferation of cells on the biodegradable suture were examined.

Test Example 2

Experiment on the Adhesion and Proliferation of Cells

1. Isolation and Culture of Umbilical Cord Blood-Derived Mesenchymal Stem Cells

Umbilical cord blood was collected from subjects under previous consent, and this study was approved by the Institutional Review Board of the Catholic University of Korea, College of Medicine [IRB No. 08-4].

Umbilical blood was centrifuged using Ficoll-Paque™ PLUS radient (GE Healthcare Bio-sciences AB, Uppsala, Sweden) at 560 g for 30 min to collect monocytes which were then washed with PBS (Welgene, Daegu, South Korea). The cells were suspended in low glucose-DMEM containing 10% FBS and 1% antibiotics/antimycotic and were cultured in a 5% $CO_2$ incubator at 37° C. After 7 days, the non-adherent cells were removed, and the adherent cells continued to be cultured. The pyramidal adherent cells were washed, detached with 0.25% trypsin EDTA and neutralized with fresh medium. $2\times10^5$ cells were placed in a 75-$cm^2$ flask and then cultured. The cells were cultured to a confluence of 75-90%, and the passage of initial cell culture was referred to as passage 1 (p1).

2. Labeling of Mesenchymal Stem Cells with Green Fluorescent Protein (GFP)

The umbilical cord blood-derived mesenchymal stem cells, isolated and cultured in Test Example 2-1 above, were labeled with green fluorescent protein (hereinafter referred to as "GFP") using a Lenti-viral vector.

The GFP-containing Lenti-viral vector was purchased from the Macrogen LentiVector Institute (Seoul, Korea).

The mesenchymal stem cells were seeded in a 6-well plate at a density of about $1\times10^5$ cells/well. The mesenchymal stem cells were infected with Lenti-GFP together with 8 µg/ml of polybrene, and after 6 hours, the medium was replaced with fresh medium, and the cells were cultured for 2-3 days. After 2-3 days, GFP in the cells was observed with a fluorescence microscope.

3. WST-1 Assay

As a control, a non-surface-treated suture was used. The control and the suture surface-treated with collage in Example were sterilized with UV light overnight. Sutures having uniform thickness and length were taken from the sterilized sutures in a clean bench and plated densely in each well of a 96-well plate. The sutures were washed and pre-wetted with PBS, and then $10^3$ cells together with 200 µl of complete media (DMEM, 10% FBS, 1% PS, Gibco, USA) were added to each well. Days 1, 3 and 7, the degree of cell proliferation was measured using WST-1 reagent and a UV spectrophotometer.

4. Observation with Fluorescence Microscope

It is difficult to examine the adhesion of cells to sutures by the Gimmesa's test that is generally used to the cell morphology. For this reason, cells with a fluorescence protein were used to measure the adhesion of cells to the sutures.

Before one day, the sutures were sterilized with UV light. Sutures having uniform thickness and length were taken from the sterilized sutures and plated densely in each well of a 96-well plate. The sutures were washed and pre-wetted with PBS, and then $10^3$ cells together with 200 µl of complete media (DMEM, 10% FBS, 1% PS 1, Gibco, USA) were added to each well. After 7 days, the cells on the surface of the sutures were observed with a fluorescence microscope.

FIG. 7 shows a comparison of cell proliferation on the non-treated control suture, the suture soaked in collagen, and the suture soaked in collagen after modification by plasma treatment. As can be seen therein, the suture modified by plasma treatment showed a significantly higher optical density than the non-treated suture and the suture soaked in collagen, indicating that the ability of cell proliferation on the suture modified by plasma treatment was significantly increased.

The cells cultured on the surface of each of the non-treated suture and the surface-treated suture in FIG. 7 for one week were observed with a fluorescence microscope, and the results of the observation are shown in FIGS. 8 and 9.

As can be seen in FIGS. 8 and 9, the GFP-labeled cells survived better on the suture surface-modified with collagen than on the non-treated suture.

From the above results, it could be seen that the surface modification of the biodegradable polymer was successfully performed and surface modification with the hydrophilic material influences the adhesion of cells. Accordingly, the cell compatible suture having the hydrophilic material introduced onto the surface of the biodegradable polymer could be provided.

As described above, the present invention provides the biodegradable suture-type cell delivery system obtained by hydrophilically modifying the surface of the biodegradable suture comprising the hydrophobic multifilament draw-textured yarn (DTY) made of the biodegradable material having the bulky structure and then bonding the cell compatible material to the surface.

Also, the biodegradable suture-type cell delivery system of the present invention has improved cell compatibility, and the bulky structure is beneficial for the proliferation of cells or living. Particularly, the biodegradable suture-type cell delivery system can improve the rate of engraftment of stem cells in vivo.

Moreover, the present invention provides the optimal method for preparing the biodegradable suture-type cell delivery system having improved cell compatibility.

In addition, the present invention provides the cell compatible suture having improved cell compatibility by modifying the surface of PLGA, a copolymer of glycolide and lactide (90:10 to 70:30 w/w), by plasma treatment.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A biodegradable suture-type cell delivery system comprising;
   a biodegradable suture containing a hydrophobic multifilament draw-textured yarn which has at least partially a bulkiness of 150-1000% and comprises a biodegradable polymer,
   wherein a surface of the hydrophobic multifilament draw-textured yarn is plasma-modified with a hydrophilic functional group-containing compound, wherein a thickness of a deposition of the hydrophilic functional group-containing compound does not exceed 100 Å on the surface of the biodegradable suture so as to enable introduction of a functional group for a secondary modification of the surface, and wherein a cell compatible material is bonded to the surface modified with the hydrophilic functional group-containing compound.

2. The biodegradable suture-type cell delivery system of claim 1, wherein the multifilament draw-textured yarn has pores of 1-150 μm.

3. The biodegradable suture-type cell delivery system of claim 1, wherein the biodegradable polymer is a homopolymer or a copolymer comprising a compound selected from the group consisting of glycolide, glycolic acid, lactide, lactic acid, caprolactone, dioxanone, trimethyl carbonate, and ethyl glycol.

4. The biodegradable suture-type cell delivery system of claim 1, wherein the biodegradable polymer is a copolymer of glycolide and lactide consisting of 90:10 to 70:30 w/w.

5. The biodegradable suture-type cell delivery system of claim 1, wherein the hydrophilic functional group is any one selected from the group consisting of an amine group, a carboxylic group and a hydroxyl group.

6. The biodegradable suture-type cell delivery system of claim 1, wherein the cell compatible material is any one selected from the group consisting of collagen, gelatin, laminin, fibronectin, galactose and chitosan.

7. A biodegradable suture comprising of;
    a biodegradable multifilament draw-textured yarn which comprises a copolymer of glycolide and lactide consisting of 90:10 to 70:30 w/w and has at least partially a bulkiness of 150-1000% and pores of 1-150 μm,
    a hydrophilic functional group-containing compound adhered on the surface of the biodegradable multifilament draw-textured yarn by a plasma enhanced chemical vapor deposition process, wherein a thickness of a deposition of the hydrophilic functional group-containing compound does not exceed 100 Å, and
    a cell compatible material bonded thereto.

8. The biodegradable suture of claim 7, wherein the hydrophilic functional group-containing compound is a hydrophilic amine compound.

9. The biodegradable suture of claim 7, wherein the cell compatible material is collagen.

* * * * *